United States Patent [19]
Arasaki et al.

[11] Patent Number: 5,472,949
[45] Date of Patent: Dec. 5, 1995

[54] N[4]-(SUBSTITUTED-OXYCARBONYL)-5'-DEOXY-5-FLUOROCYTIDINE COMPOUNDS, COMPOSITIONS AND METHODS OF USING SAME

[75] Inventors: Motohiro Arasaki; Hideo Ishitsuka; Isami Kuruma; Masanori Miwa; Chikako Murasaki; Nobuo Shimma; Isao Umeda, all of Kanagawa, Japan

[73] Assignee: Hoffmann-La Roche Inc., Nutley, N.J.

[21] Appl. No.: 167,392

[22] Filed: Dec. 14, 1993

[30] Foreign Application Priority Data

Dec. 18, 1992 [EP] European Pat. Off. ............ 92121538

[51] Int. Cl.[6] ............................ A61K 31/70; C07H 19/06
[52] U.S. Cl. ........................ 514/49; 536/28.5; 536/28.52
[58] Field of Search ...................... 514/49, 50; 536/28.5, 536/28.52

[56] References Cited

U.S. PATENT DOCUMENTS 4,966,891 10/1990 Fujiu et al. ............................ 514/49

OTHER PUBLICATIONS

Umeda et al., "Synthesis and antitumor activity of 5'-deoxy-5-fluorocytidine (5'-DFCR) derivatives", J. Pharmacobio-Dyn., 13:s-144 (1990).

Primary Examiner—Douglas W. Robinson
Assistant Examiner—James O. Wilson
Attorney, Agent, or Firm—George M. Gould; George W. Johnston; Robert A. Silverman

[57] ABSTRACT

The invention relates to N[4]-(substituted-oxycarbonyl)-5'-deoxy-5-fluorocytidine derivatives which are useful as an agent for treating tumors, pharmaceutical compositions including the same, a method of treating tumors and a method of preparing N[4]-(substituted-oxycarbonyl)-5'-deoxy-5-fluorocytidine derivatives for treating tumors.

Compounds of formula (I),

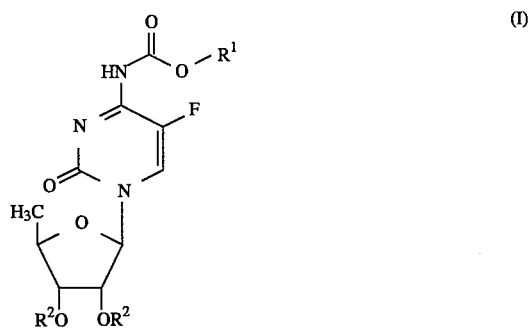

wherein $R^1$ is a saturated or unsaturated, straight or branched hydrocarbon radical wherein the number of carbon atoms in the longest straight chain of this hydrocarbon radical ranges from three to seven, or is a radical of the formula $-(CH_2)n-^Y$ wherein Y is a cyclohexyl radical, a $C_1$–$C_4$ alkoxy radical or a phenyl radical and wherein when Y is a cyclohexyl radical n is an integer from 0 to 4, and when Y is $C_1$–$C_4$ alkoxy radical or a phenyl radical n is an integer from 2 to 4, and $R^2$ is a hydrogen atom or a radical easily hydrolyzable under physiological conditions, or a hydrate or solvate thereof. Compounds of formula (I) are useful in the treatment of tumors.

6 Claims, No Drawings

$N^4$-(SUBSTITUTED-OXYCARBONYL)-5'-DEOXY-5-FLUOROCYTIDINE COMPOUNDS, COMPOSITIONS AND METHODS OF USING SAME

SUMMARY OF INVENTION

The invention relates to $N^4$-(substituted-oxycarbonyl)-5'-deoxy-5- fluorocytidine derivatives of formula (I),

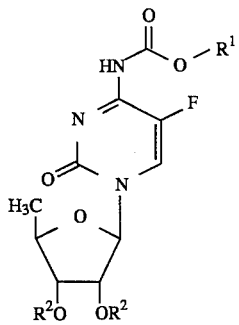

(I)

wherein $R^1$ is a saturated or unsaturated, straight or branched hydrocarbon radical wherein the number of carbon atoms in the longest straight chain of the hydrocarbon radical ranges from three to seven, or is a radical of the formula $-(CH_2)_n-Y$ wherein Y is a cyclohexyl radical, a $C_1-C_4$ alkoxy radical or a phenyl radical and n is an integer from 0 to 4; and when Y is a $C_1-C_4$ alkoxy radical or a phenyl radical n is an integer from 2 to 4, and $R^2$ is a hydrogen atom or a radical easily hydrolyzable under physiological conditions,
or a hydrate or solvate thereof. The compound is useful for treating tumors.

In another aspect, the invention relates to a pharmaceutical composition including an effective amount of at least one compound of formula (I). The pharmaceutical composition has excellent pharmacokinetic profiles for treating tumors with high safety margin.

In yet a further aspect, the invention relates to a method of treating tumors comprising administering to a host in need of such treatment an effective amount of a compound of formula (I).

In yet another aspect, the invention relates to a process for producing a N4-(substituted-oxycarbonyl)-5'-fluorocytidine derivatives which comprises reacting a compound of formula (II).

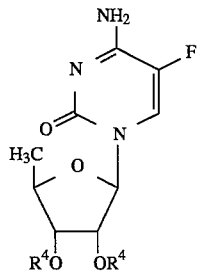

(II)

wherein $R^4$ is a hydroxy-protecting radical, with a compound of formula (III)

 (III)

and, optionally, removing $R^4$.

BACKGROUND OF THE ART

It is known that many precursors of 5-fluorouracil (5-FU) are useful as antitumor agents, but in general their bioconversion efficiency is still insufficient for the treatment of patients suffering from tumors. Further they cause intestinal toxicities and immunosuppressive toxicities, which are their major and dose limiting toxicities, respectively.

U.S. Pat. No. 4,966,891 discloses precursors of 5-FU which are improved in the above mentioned aspect of bioconversion efficiency and toxicities. They are converted to 5'-deoxy-5-fluorocytidine (5'-DFCR) by acylamidases, to 5'-deoxy-5-fluorouridine (5'-DFUR) by cytidine deaminase, and then to 5-FU by pyrimidine nucleotide phosphorylase in vivo which is preferentially localized in the liver, small intestin and tumor tissues.

DETAILED DESCRIPTION OF THE INVENTION

The invention relates to compounds of formula (I),

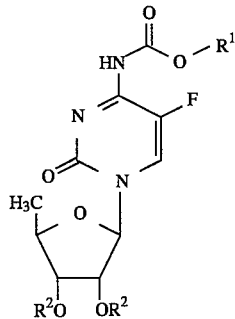

(I)

wherein $R^1$ is a saturated or unsaturated, straight or branched hydrocarbon radical wherein the number of carbon atoms in the longest straight chain of this hydrocarbon radical ranges from three to seven, or is a radical of the formula $-(CH_2)_n-Y$ wherein Y is a cyclohexyl radical, a $C_1-C_4$ alkoxy radical or a phenyl radical and wherein when Y is a cyclohexyl radical n is an integer from 0 to 4, and when Y is $C_1-C_4$ alkoxy radical or a phenyl radical n is an integer from 2 to 4, and $R^2$ is a hydrogen atom or a radical easily hydrolyzable under physiological conditions,
or a hydrate or solvate thereof. Compounds of formula (I) are useful in the treatment of tumors.

In the above, the term a saturated or unsaturated, straight or branched hydrocarbon radical wherein the number of carbon atoms in the longest straight chain of this hydrocarbon radical ranges from three to seven preferably is n-propyl, 1-isopropyl-2-methylpropyl, 1,1,2-trimethylpropyl, n-butyl, isobutyl, 2-ethylbutyl, 3,3-dimethylbutyl, n-pentyl, isopentyl, neopentyl, 2-propylpentyl, n-hexyl, 2-ethylhexyl, n-heptyl, allyl, 2-buten-1-yl, 3-buten-1-yl, 3-penten-1-yl, 4-penten-1-yl, 3-hexen-1-yl, 4-hexen-1-yl, 5-hexen-1-yl, and the like.

The term a radical of the formula $-(CH_2)_n-Y$ [in which n is an integer from 0 to 4, when Y is a cyclohexyl radical, or n is an integer from 2 to 4, when Y is a lower alkoxy radical having from 1 to 4 carbon atom(s) or a phenyl radical preferably is cyclohexyl, cyclohexylmethyl, 2-cyclohexylethyl, 3-cyclohexylpropyl, 4-cyclohexylbutyl, 2-methoxyethyl, 2-ethoxyethyl, 2-propoxyethyl, 3-methoxypropyl, 3-ethoxypropyl, 4-methoxybutyl, 4-ethoxybutyl, phenethyl, 3-phenylpropyl, 4-phenylbutyl, and the like.

Most preferably, $R^1$ is n-propyl, n-butyl, n-pentyl, isopentyl, neopentyl, 3,3-dimethylbutyl, n-hexyl, 2-ethylbutyl, phenylethyl, or cyclohexylmethyl.

In the above, the term a radical easily hydrolyzable under physiological condition preferably denotes acetyl, propionyl, benzoyl, toluoyl, β-alanyl, valyl, and the like.

Preferred $N^4$-(substituted-oxycarbonyl)-5'-DFCRs of the invention are:

5'-deoxy-5-fluoro-$N^4$-(propoxycarbonyl)cytidine, $N^4$-(butoxycarbonyl)-5'-deoxy-5-fluorocytidine, 5'-deoxy-5-fluoro-$N^4$-(pentyloxycarbonyl)cytidine, 5'-deoxy-5-fluoro-$N^4$-(hexyloxycarbonyl)cytidine, 5'-deoxy-5-fluoro-$N^4$-(isopentyloxycarbonyl)cytidine, 5'-deoxy-5-fluoro-$N^4$-(neopentyloxycarbonyl)cytidine, 5'-deoxy-5-fluoro-$N^4$-[(1,1,2-trimethylpropoxy)carbonyl]cytidine, 5'-deoxy-$N^4$-[(3,3-dimethylbutoxy)carbonyl]-5-fluorocytidine, 5'-deoxy-5-fluoro-$N^4$-[(1-isopropyl-2-methylpropoxy)carbonyl]cytidine, 5'-deoxy-$N^4$-[(2-ethylbutoxy)carbonyl]-5-fluorocytidine, $N^4$-[(cyclohexylmethoxy)carbonyl]-5'-deoxy-5-fluorocytidine, 5'-deoxy-5-fluoro-$N^4$-[(2-phenylethoxy)carbonyl]cytidine, 2',3'-di-O-acetyl-5'-deoxy-5-fluoro-$N^4$-(propoxycarbonyl)cytidine, 2',3'-di-acetyl-$N^4$-(butoxycarbonyl)-5'-deoxy-5-fluorocytidine, 2',3'-di-benzoyl-$N^4$-(butoxycarbonyl)-5'-deoxy-5-fluorocytidine, 2',3'-di-O-acetyl-5'-deoxy-5-fluoro-$N^4$-(pentyloxycarbonyl)cytidine, 2',3'-di-acetyl-5'-deoxy-5-fluoro-$N^4$-(isopentyloxycarbonyl)cytidine, 2',3'-di-O-acetyl-5'-deoxy-5-fluoro-$N^4$-(hexyloxycarbonyl)-cytidine, 2',3'-di-O-acetyl-5'-deoxy-$N^4$-[(2-ethylbutyl)oxycarbonyl]-5-fluorocytidine, 2',3'-di-O-acetyl-$N^4$-[(cyclohexylmethoxy)carbonyl]-5'-deoxy-5-fluorocytidine, 2',3'-di-O-acetyl-5'-deoxy-5-fluoro-$N^4$-[(2-phenylethoxy)carbonyl]cytidine, 5'-deoxy-5-fluoro-$N^4$-(isobutoxycarbonyl)cytidine, 5'-deoxy-5-fluoro-$N^4$-[(2-propylpentyl)oxycarbonyl]cytidine, 5'-deoxy-$N^4$-[(2-ethylhexyl)oxycarbonyl]-5-fluorocytidine, 5'-deoxy-5-fluoro-$N^4$-(heptyloxycarbonyl)cytidine, $N^4$-[(2-cyclohexylethoxy)carbonyl]-5'-deoxy-5-fluorocytidine, $N^4$-[(3-cyclohexylpropyl)oxycarbonyl]-5'-deoxy-5-fluorocytidine, $N^4$-(cyclohexyloxycarbonyl)-5'-deoxy-5-fluorocytidine, 5'-deoxy-5-fluoro-$N^4$-[(3-phenylpropyl)oxycarbonyl]cytidine, and 5'-deoxy-5-fluoro-$N^4$-[(2-methoxyethoxy)carbonyl]cytidine.

and their hydrates or solyates, and the like.

Among the above compounds, particularly preferred $N^4$-(substituted-oxycarbonyl)-5'-DFCRs of the invention are:

5'-deoxy-5-fluoro-$N^4$-(propoxycarbonyl)cytidine,

5'-deoxy-5-fluoro-$N^4$-(isopentyloxycarbonyl)cytidine,

5'-deoxy-5-fluoro-$N^4$-(hexyloxycarbonyl)cytidine,

5'-deoxy-$N^4$-[(2-ethylbutyl)oxycarbonyl]-5-fluorocytidine,

5'-deoxy-5-fluoro-$N^4$-(neopentyloxycarbonyl)cytidine,

5'-deoxy-$N^4$-[(3,3-dimethylbutoxy)carbonyl]-5-fluorocytidine,

5'-deoxy-5-fluoro-$N^4$-[(2-phenylethoxy)carbonyl]cytidine, $N^4$-[(cyclohexylmethoxy)carbonyl]-5'-deoxy-5-fluorocytidine, specially $N^4$-(butoxycarbonyl)-5'-deoxy-5-fluorocytidine, 5'-deoxy-5-fluoro-$N^4$-(pentyloxycarbonyl)cytidine, and their hydrates or solvates, and the like.

Studies on the pharmacokinetic profiles of the precursors of 5-FU, particularly of $N^4$-(substituted-oxycarbonyl)-5'-deoxy-5-fluorocytidine derivatives, showed that certain specific precursors are selectively converted into 5'-DFCR by an acylamidase isozyme that is preferentially located at the liver but not the other organs of humans, and exhibited more improved pharmacokinetic profiles than the other compounds tested. Further studies based on the above findings enabled identification that the specific $N^4$-(substituted-oxycarbonyl)-5'-deoxy-5- fluorocytidine derivatives (hereinafter referred to as $N^4$-(substituted-oxycarbonyl)-5'-DFCR) of formula (I) have selectively im pharmacokinetic profiles in monkeys, that is, 4 to 7 times higher maximum concentration ($C_{max}$) of 5'-DFUR and 4 times larger higher area under the curve (AUC) of 5'-DFUR in blood than the other compounds, and less intestinal toxicity.

The $N^4$-(substituted-oxycarbonyl)-5'-DFCRs of formula (I) as well as their hydrates or solvates can be prepared by a reaction of a compound of formula (II),

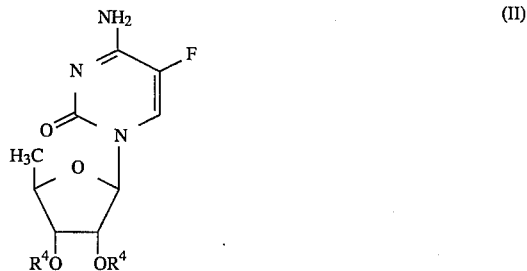

(II)

wherein $R^4$ is a hydroxy-protecting radical such as acetyl, benzoyl, trimethylsilyl, tert-butyldimethylsilyl, and the like, with a compound of formula (III),

(III)

wherein $R^1$ is the same as defined above,
followed, if necessary, by removal of a protecting radical.

The compounds of formula (II) can be prepared by 2',3'-di-O-acylation or silylation of 5'-deoxy-5-fluorocytidine [J. Med. Chem., 22, 1330 (1979)] as described in U.S. Pat. No. 4,966,891 or by direct coupling of 5-fluorocytosine with 1,2,3-tri-O-acetyl-5-deoxyribofuranose according to the procedure similar to that described in Synthesis, 748 (1981).

The reaction of the compound of formula (II) with the compound of formula (III) can be carried out in a solvent such as pyridine, dioxane, tetrahydrofuran, acetonitrile, chloroform, dichloromethane and the like in the presence of acid acceptor such as triethylamine, pyridine, picoline, 4-(N,N-dimethylamino)pyridine, lutidine and the like. The reaction can be carried out at a temperature between 0° and 30° C.

The protecting radical may, if necessary, be removed after the reaction by the procedures known to those skilled in the art [*Protective Groups in Organic Synthesis*, John Wiley & Sons, New York, *Can. J. Chem.*, 49, 493 (1971) and U.S. Pat. No. 4,966,891], for example by basic or acidic hydrolysis.

The compounds of formula (I) can exist as unsolvated as well as solvated forms, including hydrated forms. The hydration can be effected in the course of the manufacturing process or can occur gradually as a result of hygroscopic properties of an initially anhydrous product. Solyates with pharmaceutically acceptable solvents such as ethanol can be obtained during, for example, crystallization.

$N^4$-(Substituted-oxycarobonyl)-5'-DFCR derivatives of formula (I) as well as hydrates or solyates thereof prepared by the above process exhibit activity against human colon cancer CXF280 and gastric cancer GXF97 xenografts, mouse colon 26 carcinoma, mouse Lewis lung carcinoma, and the like in mice over a very wide range of dosages both orally and parenterally and are useful as antitumor agents. They are efficiently converted to 5'-DFCR by an acylamidase isozyme, to 5'-DFUR by cytidine deaminase and then to the active metabolite 5-FU by pyrimidine nucleoside phosphorylase.

The invention further relates to a pharmaceutical composition for the treatment of tumors. The pharmaceutical composition comprises an effective amount of one or more compounds of formula (I).

The $N^4$-(substituted-oxycarbonyl)-5'-DFCRs of the invention can be administered orally or non-orally to hosts by various conventional administration methods. Moreover, the $N^4$-(substituted-oxycarbonyl)-5'-DFCRs according to the invention are used singly or formulated with a compatible pharmaceutical carrier material. This carrier material can be an organic or inorganic inert carrier material suitable for enteral, percutaneous or parenteral administration such as, water, gelatin, gum arabic, lactose, starch, magnesium stearate, talc, vegetable oils, polyalkylene-glycols or petroleum jelly. The pharmaceutical composition can be made up in a solid form, for example, as tablets, dragees, enteric coating tablets, granulars, enteric coating granulars, suppositories, capsules or enteric capsules, in a semi-solid form, for example, as salves, or in a liquid form, for example, as solutions, suspensions or emulsions. The pharmaceutical composition may be sterilized and/or may contain further adjuvants such as preserving, stabilizing, setting or emulsifying agents, flavor-improving agents, salts for variation of the osmotic pressure or substances acting as buffers. The pharmaceutical composition can be prepared in a conventional manner.

The $N^4$-(substituted-oxycarbonyl)-5'-DFCRs according to the present invention can be used alone or as mixtures of two or more different $N^4$-(substituted-oxycarbonyl)-5'-DFCRs and the amount of the $N^4$-(substituted-oxycarbonyl)-5'-DFCRs is about 0.1 to 99.5%, preferably 0.5 to 95%, based on the weight of the pharmaceutical composition.

The pharmaceutical composition according to the present invention may be formulated in a combination with other conventional antitumor agent.

The invention also relates to a method of treating tumors comprising administering to a host in need of such treatment an effective amount of at least one compound of formula (I).

Susceptibility to acylamidase of the $N^4$-(substituted-oxycarbonyl)- 5'-DFCRs of the invention and their pharmacokinetic profil monkey are shown below:

1. Susceptibility to human and monkey acylamidases

The $N^4$-(substituted-oxycarbonyl)-5'-DFCRs of the invention were incubated with crude extracts of monkey and human liver in the presence of an inhibitor of cytidine deaminase, tetrahydrouridine (0.4 mM) at 37° C. for 60 min. Thereafter, the product 5'-DFCR was separated by HPLC and the enzyme susceptibility was calculated from the amount of the product. As Table 1 shows, the compounds of formula (I) were highly susceptible to the human liver acylamidase, suggesting that they are efficiently biotransformed to 5'-DFCR in human.

TABLE 1

Susceptibility to monkey and human acylamidase in the liver

| Compound (Example No.) | Acylamidase activity (nmol/mg protein/hr) | |
| --- | --- | --- |
| | Monkey Liver | Human Liver |
| 11 | 20 | 71 |
| 12 | 29 | 190 |
| 13 | 47 | 220 |
| 14 | 32 | 74 |
| 15 | 23 | 210 |
| 16 | 33 | 210 |
| 17 | 22 | 160 |
| 20 | 19 | 320 |
| 21 | 26 | 82 |
| 22 | 43 | 110 |
| 24 | 18 | 64 |
| 25 | <13 | 160 |
| 26 | 20 | 560 |
| 27 | 59 | 110 |
| 28 | 25 | 52 |
| 29 | 22 | 50 |

2. Pharmacokinetic profiles in monkeys

The compounds of formula (I) were orally administered into groups of 2 to 5 cynomolgous monkeys (3–4 kg). At various times after the administration, plasma was taken for determination of blood concentrations of intact molecules and their active metabolite 5'-DFUR.

Metabolites in the plasma were separated by HPLC and their concentrations were calculated. As Table 2 shows, the compounds of the present invention gave high levels in $C_{max}$ and AUC of the active metabolite 5'-DFUR in the plasma. These results indicate that the compounds of the invention can be effectively utilized for the treatment of various tumors in human beings.

TABLE 2

Pharmacokinetic Profiles in Monkeys

| Compound (Example No.) | Plasma 5'-DFUR | |
| --- | --- | --- |
| | Cmax (μg/ml) | AUC (μg · hr/ml) |
| 10 | 1.44 | 2.03 |
| 11 | 1.57 | 2.06 |
| 12 | 2.10 | 2.90 |
| 13 | 1.50 | 1.96 |
| 14 | 1.80 | 2.40 |
| 15 | 2.60 | 2.89 |
| 16 | 1.40 | 2.52 |
| 17 | 1.65 | 2.66 |
| 28 | 1.00 | 1.40 |
| 29 | 2.00 | 2.09 |

The antitumor activities of the compounds of the invention are shown as follows:

3. Antitumor testing against human colon cancer xenograft CXF280

CXF280 tumor (about 2×2 mm piece) was implanted subcutaneously into BALB/c nu/nu mice (21–22 g) on day 0. When tumor volume became 100 mm³ on day around 14, the compounds of the invention were orally administered daily for 3 weeks. At one day after the last treatment, tumor volume was calculated.

TABLE 3

Antitumor Effects of Fluorinated Pyrimidines in BALB/c nu/nu Mice Bearing CXF280 Human Colon Carcinoma

| Compound (Example No.) | Dose × 21 (mmol/kg/day) | % Growth inhibition | Fecal observation* |
|---|---|---|---|
| Exp. 1 | | | |
| Vehicle | — | | N |
| 12 | 0.13 | 68 | |
|  | 0.3 | 69 | |
|  | 0.67 | 86 | |
|  | 1.0 | 86 | |
|  | 1.5 | 96 | N |
| 13 | 0.13 | 59 | |
|  | 0.3 | 66 | |
|  | 0.67 | 79 | |
|  | 1.0 | 91 | |
|  | 1.5 | 94 | N |
| 24 | 0.13 | 37 | |
|  | 0.3 | 64 | |
|  | 0.67 | 75 | |
|  | 1.0 | 83 | |
|  | 1.5 | 89 | N |
| Reference compound | | | |
| 5-FU | 0.089 | 28 | N |
|  | 0.13 | 59 | N |
|  | 0.2 | 79 | L |
| Exp. 2 | | | |
| Vehicle | — | | N |
| 10 | 0.13 | 39 | |
|  | 0.3 | 56 | |
|  | 0.67 | 75 | |
|  | 1.5 | 86 | |
|  | 2.25 | 93 | N |
| 11 | 0.13 | 46 | |
|  | 0.3 | 72 | |
|  | 0.67 | 84 | |
|  | 1.5 | 95 | |
|  | 2.25 | 100 | N |
| 14 | 0.13 | 68 | |
|  | 0.3 | 68 | |
|  | 0.67 | 85 | |
|  | 1.5 | 94 | N |
|  | 2.25 | 100 | N |
| 27 | 0.13 | 26 | |
|  | 0.3 | 72 | |
|  | 0.67 | 84 | |
|  | 1.5 | 94 | N |
|  | 2.25 | 103 | N |
| Reference compound | | | |
| 5-FU | 0.089 | NE | N |
|  | 0.13 | 20 | N |
|  | 0.2 | 58 | L |

NE: Not Effective,
*Fecal observation (N: normal feces, L: loose passage)

The percent inhibition of tumor growth given in Table 3 above was calculated from the formula:

$$\% \text{ Inhibition} = \{1-(T-V_0)/(C-V_0)\} \times 100$$

$V_0$=volume of tumor before treatment was started, T=volume of the tumors from the treated group, C=volume of the tumor from the control group.

As Table 3 shows, the compounds provided in the present invention were safely administered without causing intestinal toxicity and were much more effective than 5-FU.

4. Antitumor and anticachexia activity against mouse colon 26 carcinoma

Antitumor activity of a representative compound (Example 13), of the present invention, was measured as follows. Mice ($CDF_1$) were subcutaneously inoculated with colon 26 carcinoma ($10^6$ cells) on day 0. The compound was administered daily for 7 times from day 21 when the animals became cachectic. One day after the last treatment, tumor weight gain, carcass weight gain, adipose tissue weight, concentrations of glucose and the acute phase reactant IAP (immunosuppressive acidic protein) in the serum were measured. As Table 4 shows, mice treated with vehicle were abnormal in cachexia parameters such as adipose tissue weight, serum glucose and IAP levels, whereas treatment with the compound of Example 13 suppressed tumor growth and improved cachexia.

TABLE 4

Improvement of Tumor Cachexia with Fluorinated Pyrimidines in Mice Bearing Colon 26 Adenocarcinoma

| Compound (Example No.) | Dose × 7 (mmol/ kg) (μg/ml) | Tumor wt. change (g) | Carcass wt. change (g) | Adipose tissue wt. (mg) | Serum glucose (mg/dl) | Serum IAP |
|---|---|---|---|---|---|---|
| Vehicle | | 1.65 | −1.5 | 11 | 91 | 1167 |
| 13 | 0.125 | 1.24 | 1.6* | 22* | 118* | 1195 |
|  | 0.25 | 0.91 | 3.4* | 42* | 120* | 1020 |
|  | 0.5 | 0.79* | 4.2* | 63* | 147* | 805* |
|  | 1 | 0.006 | 5.6* | 85* | 127* | 795* |

*P < 0.05 versus corresponding value of vehicle group

The toxicity ($LD_{50}$) of the representative compounds (Example 13,14, and 17) of the present invention was examined by oral administration daily for 21 days in mice. The representative $LD_{50}$ values obtained from the experiments were more than 500 mg/kg/day.

A dosage per day to a patient of the $N^4$-(substituted-oxycarbonyl)-5'-DFCRs of the present invention may be varied depending upon his weight and state to be remedied, but generally is in the range of 0.5 to 500 mg per 1 kg of weight, preferably about 2 to 200 mg. It should be noted that the compound of the invention can be expected to have 3–5 times higher activity than those of the compounds disclosed in U.S. Pat. No. 4,966,891 in humans, when taking into consideration of the data of $C_{max}$ and AUC of 5'-DFUR after oral administration of the present compounds in monkeys. From the same reason, the compounds of the present invention can be expected to show sufficient activity at the 3–5 times lower dosage than those of the compounds of U.S. Pat. No. 4,966,891. The present invention can provide a pharmaceutical composition for treating tumors with high safety margin.

The following Examples are intended to illustrate the present invention in more detail, but are not intended to limit its scope in any manner.

Reference example: Preparation of starting material
Preparation of 2',3'-di-O-acetyl-5'-deoxy-5-fluorocytidine
(a) From 5'-deoxy-5-fluorocytidine 5'-Deoxy-5-fluorocytidine (50 mg) was dissolved in dry pyridine (1.3 ml). To the solution was added acetic anhydride (39 ml) with stirring at 0° C. The reaction mixture was stirred for 3 hours at 0° C. After removal of the solvent under reduced pressure, the residue was partitioned between ethyl acetate and ice cooled water. The ethyl acetate layer was dried over magnesium sulfate and concentrated under reduced pressure. The residue was purified by silica gel column chromatography (dichloromethane/methanol=9/1 as an eluent) followed by recrystallization from isopropanol to give 37 mg of 2',3'-di-O-acetyl-5'-deoxy-5-fluorocytidine: 191.5°–193° C., FAB-MS m/z 330 (MH$^+$).

(b) From 5-fluorocytosine and 1,2,3-tri-O-acetyl-5-deoxy-β-D-ribofuranose

A solution of sodium iodide (3.6 g) and chlorotrimethylsilane (794 ml) in dry acetonitrile (15 ml) was stirred with molecular sieves 4A (200 mg) at 0° C. for 5 minutes (colorless sodium chloride deposited during stirring). 1,2,3-Tri-O-acetyl-5-deoxy-β-D-ribofuranose (2.0 g) was added and the mixture was stirred at 0° C. for 30 min. Then, a solution of the trimethylsilylated 5-fluorocytosine, freshly prepared from 5-fluorocytosine (1.12 g), in dry acetonitrile (5 ml) was added at 0° C. and stirring was continued for 3 h at room temperature. The mixture was filtered, the filtrate was concentrated in vacuo, and the residue was partitioned between dichloromethane and saturated aq. sodium bicarbonate solution. The aqueous layer was extracted with $CH_2Cl_2$/MeOH (10:1). The combined organic layers were dried over anhydrous sodium sulfate and evaporated under reduced pressure. The residue was purified by silica gel chromatography using $CH_2Cl_2$/MeOH (15:1) as an eluent, followed by recrystallization from isopropanol to give 1.24 g of 2',3'-di-O-acetyl-5'-deoxy-5-fluorocytidine.

Example 1

Preparation of 2',3'-di-O-acetyl-5'-deoxy-5-fluoro-N$^4$-(propoxycarbonyl)cytidine To a solution of 2',3'-di-O-acetyl-5'-deoxy-5-fluorocytidine (2 g) in $CH_2Cl_2$ (15 ml) and dry pyridine (983 ml) was added dropwise n-propyl chloroformate (957 ml) with stirring and cooling on ice bath. After stirring for 30 min at room temperature, the mixture was evaporated to dryness under reduced pressure. The residue was partitioned between ether and saturated aqueous solution of sodium bicarbonate. The organic layer was washed with brine, dried over anhydrous sodium sulfate and filtered.

The filtrate was evaporated to give 2',3'-di-O-acetyl-5'-deoxy-5- fluoro-N$^4$-(propoxycarbonyl)cytidine (2.5 g) :EI-MS m/z 415(M$^+$); $^1$H-NMR(d$_6$-DMSO) δ0.92 (3H, t, J=7.3 Hz), 1.37 (3H, d, J=6.3 Hz), 1.63 (2H, sex, J=7.3 Hz), 4.06–4.14 (3H, m), 5.11 (1H, t, J=6.3 Hz), 5.47 (1H, d.d., J=4.6 & 6.3 Hz), 5.81 (1H, d, J=4.6 Hz), 8.31 (1H, br. s), 10.63 (1H, br. s)

The following compounds were obtained according to a manner analogous to that of Example 1. The compound of Example 9 was prepared from the known 2',3'-di-O-benzoyl-5'-deoxy-5-fluorocytidine (U.S. Pat. No. 4,966,891) by the similar manner to that of Example 1.

| Example No. | R$^1$ | R$^2$ | $^1$H-NMR (in solvent 1 or 2) | FAB-MS (m/z) |
|---|---|---|---|---|
| 2 | n-butyl | acetyl | δ(1): 0.87(3H, t, J=7.3Hz), 1.36(5H, m), 1.59(2H, m), 2.05(3H, s), 2.07(3H, s), 4.12(3H, m), 5.11(1H, br.t), 5.47(1H, br, t), 5.81(1H, d, J=4.3Hz), 8.34 (1H, br.s), 10.60(1H, br.s) | 430(MH$^+$) |
| 3 | n-pentyl | acetyl | δ(1): 0.88(3H, t, J=7.3Hz), 1.31(5H, m), 1.36 (3H, d, J=6.3Hz), 1.61(1H, m), 2.06(3H, s), 2.07(3H, s), 4.07–4.14(3H, m), 5.11(1H, t, J=6.3Hz), 5.47(1H, d.d, J=6.3 & 4.6Hz), 5.80(1H, d, J=4.6Hz), 8.28(1H, br.s), 10.63(1H, br.s) | 444(MH+) |
| 4 | n-hexyl | acetyl | δ(1): 0.87(3H, t, J=6.9Hz), 1.30(6H, m), 1.36(3H, d, J=6.3Hz), 1.59(2H, m), 2.06(3H, s), 2.07(3H, s), 4.07–4.14(3H, m), 5.11(1H, t, J=6.3Hz), 5.45(1H, d.d, J=6.3 & 4.6Hz), 5.80(1H, d, J=4.6Hz), 8.28(1H, br s), 10.63(1H, br.s) | 458(MH+) |
| 5 | isopentyl | acetyl | δ(1): 0.90(6H, d, J=6.9Hz), 1.36(3H, d, J=6.3Hz), 1.51 (2H, q, J=6.9Hz), 1.68(1H, m), 2.06(3H, s), 2.07 (3H, s), 4.09–4.20(3H, m), 5.11(1H, t, J=6.3Hz), 5.46(1H, d.d, J=6.3 & 4.3Hz), 5.80(1H, d, J=4.3Hz), 8.28(1H, br.s), 10.63(1H, br.s) | 444(MH+) |
| 6 | 2-ethylbutyl | acetyl | δ(1): 0.87(6H, t, J=7.3Hz), 1.23–1.45(7H, m), 1.51(1H, m), 2.06(3H, s), 2.07(3H, s), 4.04 (2H, br.d), 4.12(1H, t, J=6.3Hz), 5.11(1H, t, J=6.3Hz), 5.46(1H, d.d., J=6.3 & 4.6Hz), 5.81 (d, J=4.6Hz), 8.32(1H, br.s), 10.61(1H, br.s) | 458(MH+) |
| 7 | cyclohexyl-methyl | acetyl | δ(1): 1.00(2H, m), 1.11–1.29(4H, m), 1.36(3H, d, J=6.3Hz), 1.57–1.77(5H, m), 2.06(3H, s), 2.07 (3H, s), 3.92(2H, br.s), 4.12(1H, m), 5.11(1H, t, J=6.3Hz), 5.46(1H, d.d, J=6.3 & 4.0Hz), 5.81(1H, d, J=4.0Hz), 8.33(1H, br.s), 10.61(1H, br.s) | 470(MH+) |
| 8 | phenethyl | acetyl | δ(1): 1.36(3H, d, J=6.3Hz), 2.06(3H, s), 2.07 (3H, s), 2.94(2H, t, J=6.8Hz), 4.12(1H, m), 4.32 (2H, br.t), 5.11(1H, t, J=6.3Hz), 5.46(1H, d.d, J=6.3 & 4.3Hz), 5.81(1H, d, J=4.3Hz), 7.16–7.37 (5H, m), 8.32(1H, br.s), 10.67(1H, br.s) | 478(MH+) |
| 9 | n-butyl | benzoyl | δ(2): 0.95(3H, t, J=7.3Hz), 1.42(2H, m) 1.58 (3H, d, J=6.3Hz), 1.68(2H, m), 4.16(2H, br.s), 4.52(1H, d.q, J=5.8 & 6.3Hz), 5.40(1H, t, J=5.8Hz) 5.65(1H, d.d, J=4.6 & 5.8Hz), 6.16(1H, d, J=4.6Hz), 7.35–7.98(11H, m), 11.9(1H, br.s) | 554(MH+) |

NMR: solvent 1 = d$_6$-DMSO, Solvent 2 = CDCl$_3$

Example 10

Preparation of 5'-deoxy-5-fluoro-$N^4$-(propoxycarbonyl)cytidine

To a solution of 2',3'-di-O-acetyl-5'-deoxy-5-fluoro-$N^4$-(propoxycarbonyl)cytidine (2.5 g) in $CH_2Cl_2$ (17 ml) was added dropwise 1N NaOH (17 ml) with stirring and cooling with ice bath. After stirring for 1 hr at 0° C., MeOH (0.9 ml) was added to the mixture. And pH of the reaction mixture was adjusted to 6 by the addition of concentrated HCl and partitioned. The aqueous layer was extracted with a mixed solvent of $CH_2Cl_2$/MeOH(95/5) successively (40 ml×10). The combined organic layers were dried over anhydrous sodium sulfate and filtered. The solution was evaporated, and the residue was crystallized from ethyl acetate to give 5'-deoxy-5-fluoro-$N^4$-(propoxycarbonyl)cytidine as colorless crystals (1.6 g, y. 79.8%): mp. 125°–126.5° C.; EI-MS m/z 331 ($M^+$).

The following compounds were obtained according to a manner analogous to that of Example 10.

| Example No. | $R^1$ | $R^2$ | Melting point (°C.) | Recrystallization solvent | FAB-MS m/z |
|---|---|---|---|---|---|
| 11 | n-butyl | H | 119–120 | AcOEt | 346($MH^+$) |
| 12 | n-pentyl | H | 110–121 | AcOEt | EI 359($M^+$) |
| 13 | n-hexyl | H | 114–116 | AcOEt | EI 373($M^+$) |
| 14 | isopentyl | H | 119–120 | AcOEt | 360($MH^+$) |
| 15 | 2-ethylbutyl | H | amorphous* | — | 374($MH^+$) |
| 16 | cyclohexyl-methyl | H | 126–127 | AcOEt | 386($MH^+$) |
| 17 | phenethyl | H | 144–145 | AcOEt—MeOH | 394($MH^+$) |
| 18 | allyl | H | 118.5–120 | AcOEt | 330($MH^+$) |

*$^1$H-NMR($d_6$-DMSO) of Example 15: δ 0.87(6H, t, J=7Hz), 1.25–1.45(7H, m), 1.53(1H, m), 3.68(1H, q., J=6 Hz), 3.89(1H, br. t, J=6Hz), 4.02(2H, d, J=6Hz), 4.10(1H, m), 5.05(1H, d, J=6Hz), 5.4(1H, d, J=6Hz), 5.67(1H, d, J=3Hz), 8.00(1H, br. s), 10.55 & 11.60 (total 1H, br. s each).

Example 19

Preparation of $N^4$-(cyclohexyloxycarbonyl)-5'-deoxy-5-fluorocytidine

5'-Deoxy-5-fluorocytidine (2.5 g) was dissolved in dry pyridine (20 ml). To the mixture, trimethylsilyl chloride (3.4 ml) was added dropwise at 0° C., and stirred for 30 min at room temperature. To the reaction mixture, cyclohexyl chloroformate (2.0 ml) was added in one portion at 0° C. After stirring of the mixture for 1 hour at room temperature, pyridine was evaporated under reduced pressure. The residue was then partitioned between saturated aqueous $NaHCO_3$ and ether. The organic layer was washed with brine, dried over anhydrous $MgSO_4$ and concentrated under reduced pressure. To the residue were added citric acid (2.0 g) and methanol (50 ml). The mixture was stirred at room temperature overnight. After removal of the solvent under reduced pressure, the residue was dissolved in $CH_2Cl_2$/MeOH (95:5) and neutralized by aqueous NaOH. The organic layer was dried over anhydrous $Na_2SO_4$ and concentrated under reduced pressure. The residue was purified by silica gel chromatography using $CH_2Cl_2$/MeOH (20:1) as an eluent, followed by recrystallization from ethyl acetate to give $N^4$-(cyclohexyloxycarbonyl)-5'-deoxy-5-fluorocytidine (3.47 g:92% yield):mp. 134°–136° C., FAB-MS m/z 372 ($MH^+$).

The following compounds were obtained according to a manner analogous to that of Example 19.

| Example No. | $R^1$ | $R^2$ | Melting point (°C.) | Recrystallization solvent | FAB-MS m/z |
|---|---|---|---|---|---|
| 20 | 2-cyclohexylethyl | H | 128–129.5 | AcOEt | 400($MH^+$) |
| 21 | 3-cyclohexylpropyl | H | amorphous* | — | 414($MH^+$) |
| 22 | 3-phenylpropyl | H | 120–121 | AcOEt | 408($MH^+$) |
| 23 | 2-methoxyethyl | H | amorphous* | — | 348($MH^+$) |
| 24 | isobutyl | H | 132–134 | AcOEt | 346($MH^+$) |
| 25 | 2-propylpentyl | H | 116–118 | AcOEt | 402($MH^+$) |
| 26 | 2-ethylhexyl | H | amorphous** | — | 402($MH^+$) |
| 27 | n-heptyl | H | 115.5–117.5 | AcOEt | 388($MH^+$) |

*$^1$H-NMR($d_6$-DMSO) of Example 21:
δ 0.78–0.93(2H, m), 1.15–1.27(6H, m), 1.31(3H, d, J=7Hz), 1.59–1.75(7H, m), 3.68(1H, q, J=6Hz), 3.89(1H, br. t, J=6Hz), 4.01–4.14(3H, m), 5.04(1H, d, J=6Hz), 5.40(1H, d, J=6Hz), 5.67(1H, d, J=2Hz), 8.00(1H, br. s), 10.03 & 10.53(total 1H, br. s each).

**$^1$H-NMR($d_6$-DMSO) of Example 23:
δ 1.31(3H, d, J=5.9Hz), 3.28(3H, s), 3.56(2H, br. t), 3.69(1H, t, J=6Hz), 3.89(1H, m), 4.06(1H, m), 4.22(2H, br. t), 5.05(1H, d, J=6Hz), 5.40(1H, br. s), 5.67(1H, d, J=3Hz), 8.06(1H, br. s), 10.65(1H, br. s).

***$^1$H-NMR($d_6$-DMSO) of Example 26:
δ 0.85–0.88(6H, m), 1.27–1.38(11H, m), 1.57(1H, br. d, J=6Hz), 3.68(1H, q, J=6Hz), 3.89–4.02(4H, m), 5.05(1H, br. s), 5.41(1H, br. s), 5.67(1H, d, J=3Hz), 8.06(1H, br. s), 10.52(1H, br. s).

Example 28

Preparation of 5'-deoxy-5-fluoro-$N^4$-(neopentyloxycarbonyl)cytidine

5'-Deoxy-2',3'-di-O-acetyl-5-fluorocytidine (1.5 g) and dry pyridine (0.74 ml) were dissolved in dry dichloromethane (15 ml). To the mixture, toluene solution of neopentyl chloroformate (3 eq.) was added dropwise at 0° C., and stirred at room temperature for 1 hour. After the solvent was removed under reduced pressure, the residue was partitioned between ether and saturated aqueous solution of sodium carbonate. The organic layer was successively washed with water and brine, dried over anhydrous sodium sulfate and concentrated under reduced pressure to give crude 2',3'-di-O-acetyl-5'-deoxy-5-fluoro-$N^4$(neopentyloxycarbonyl)cytidine as pale yellow oil. This crude product was dissolved in ethanol (15 ml) and cooled on ice-bath. Then 1N aqueous sodium hydroxide solution was added dropwise while maintaining the temperature below 15° C. After the addition was completed, the reaction mixture was neutralized with concentrated. hydrochloric acid at 0° C. The solution was concentrated under reduced pressure, and the concentrate was partitioned between water and a mixed solution of $CH_2Cl_2$/MeOH (95:5). The aqueous layer was back-extracted with $CH_2Cl_2$/MeOH (95:5) ten times (20 ml each). All organic layers were combined, dried over anhydrous sodium sulfate and concentrated under reduced pressure. The residue was purified by silica gel column chromatography using $CH_2Cl_2$/MeOH (20:1) as an eluent to give 5'-deoxy-5-fluoro-$N^4$-(neopentyloxycarbonyl)cytidine (1.37 g: 84% yield) as amorphous powder: FAB-MS m/z 360 (MH$^+$); $^1$H-NMR (d$_6$-DMSO) δ0.93 (9H, s), 1.31 (3H, d,J=6.3 Hz), 3.68 (1H,q,J=5.9 Hz), 3.81 ( 2H, br. s), 3.87–3.92 (1H, m), 4.04–4.09 (1H, m), 5.05 (1H,d, J=5.9 Hz), 5.41 ( 1H, br. d, J=5.3 Hz), 5.67 (1H,dd,J=1.3, 3.6 Hz), 8.04 (1H, br. s), 10.53 (~1H, br. s).

Example 29

Preparation of 5'-Deoxy-$N^4$-[(3,3-dimethylbutoxy)carbonyl]-5-fluorocytidine

5'-Deoxy-$N^4$-[(3,3-dimethylbutoxy)carbonyl]-5-fluorocytidine was obtained according to a manner analogous to that of Example 28 except that 3,3-dimethylbutyl chloroformate was used as the acylating agent:amorphous powder (71% yield); FAB-MS m/z 374 (MH$^+$); $^1$H-NMR (d$_6$-DMSO) δ0.93 (9H, s), 1.31 (3H,d,J=6.3 Hz), 1.55 (2H, t,J=7.3 Hz), 3.68 (1H,q,J=5.9 Hz), 3.84–3.93 (1H, m), 4.03–4.09 (1H, m), 4.15 (2H,t,J= 7.3 Hz), 5.05 (1H,d,J=5.9 Hz), 5.40 (1H, br, d,J=5.3 Hz), 5.67 (1H,dd,J=1.3, 4.0 Hz), 8.00 (1H, br. s), 10.53 (~1H, br. s).

The following examples illustrate pharmaceutical preparations containing a compound provided by the present invention.

Example A

Interlocking gelatin capsules each containing the following ingredients were manufactured in a manner known per se:

| | |
|---|---|
| $N^4$-(Butoxycarbonyl)-5'-deoxy-5-fluorocytidine | 100 mg |
| Corn starch | 20 mg |
| Titanium dioxide | 385 mg |
| Magnesium stearate | 5 mg |
| Film | 20 mg |
| PEG 6000 | 3 mg |
| Talc | 10 mg |
| | 543 mg |

Example B

Tablets each containing the following ingredients were manufactured in a manner known per se:

| | |
|---|---|
| $N^4$-(Butoxycarbonyl)-5'-deoxy-5-fluorocytidine | 100 mg |
| Lactose | 25 mg |
| Corn starch | 20.2 mg |
| Hydroxypropylmethyl cellulose | 4 mg |
| Magnesium stearate | 0.8 mg |
| Film | 10 mg |
| PEG 6000 | 1.5 mg |
| Talc | 4.5 mg |
| | 166 mg |

Example C

Dry parenteral dosage forms were manufactured in a manner known per se:
(1) A total 5 g of $N^4$-(butoxycarbonyl)-5'-deoxy-5-fluorocytidine was dissolved in 75 ml of distilled water, the solution was subjected to a bacteriological filtration, and then divided aseptically into 10 sterile vials. The solution was then freeze-dried to yield 500 mg of sterile dry solid per vial.
(2) Clean $N^4$-(butoxycarbonyl)-5'-deoxy-5-fluorocytidine in the amount of 500 mg per vial or ampoule was sealed in the receptacle and heat-sterilized.

The above dry dosage forms were reconstituted before use by adding a suitable sterile aqueous solvent such as water for injection or isotonic sodium chloride or 5% dextrose for parenteral administration.

We claim:

1. A compound of formula (I),

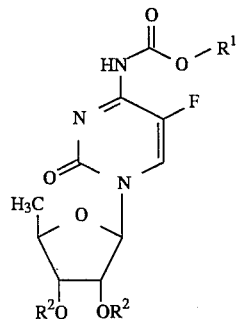

wherein $R^1$ is a saturated straight or branched hydrocarbon radical wherein the number of carbon atoms in the longest straight chain of this hydrocarbon radical ranges from three to seven, or is a radical of the formula —(CH$_2$)n—$^Y$ wherein Y is a cyclohexyl radical, a $C_1$–$C_4$ alkoxy radical or a phenyl radical and wherein when Y is a cyclohexyl radical n is an integer from 0 to 4, and when Y is $C_1$–$C_4$ alkoxy radical or a phenyl radical n is an integer from 2 to 4, and $R^2$ is a hydrogen atom or a radical easily hydrolyzable under physiological conditions,
or a hydrate or solvate thereof.

2. The compounds according to claim 1, wherein $R^1$ is selected from the group consisting of n-propyl, 1-isopropyl-2-methylpropyl, 1,1,2-trimethylpropyl, n-butyl, isobutyl, 2-ethylbutyl, 3,3-dimethylbutyl, n-pentyl, isopentyl, neopentyl, 2-propylpentyl, n-hexyl, 2-ethylhexyl, n-hetpyl, cyclohexyl, cyclohexylbutyl, 2-methoxyethyl, 2-ethoxyethyl, 3-methoxypropyl, 3-ethoxypropyl, 4-methoxybutyl, 4-ethoxybutyl, phenethyl, 3-phenyl-propyl and 4-phenylbutyl.

3. The compounds according to claim 1, selected from a group consisting of:

5'-deoxy-5-fluoro-$N^4$-(propoxycarbonyl)cytidine,
5'-deoxy-5-fluoro-$N^4$-(hexyloxycarbonyl)cytidine,
5'-deoxy-5-fluoro-$N^4$-(isopentyloxycarbonyl)cytidine,
5'-deoxy-5-fluoro-$N^4$-(neopentyloxycarbonyl)cytidine,
5'-deoxy-5-fluoro-$N^4$-[(1,1,2-trimethylpropoxy)carbonyl]cytidine,
5'-deoxy-$N^4$-[(3,3-dimethylbutoxy)carbonyl]-5-fluorocytidine,
5'-deoxy-5-fluoro-$N^4$-[(1-isopropyl-2-methylpropoxy)carbonyl]cytidine,
5'-deoxy-$N^4$-[(2-ethylbutyl)oxycarbonyl]-5-fluorocytidine,
$N^4$-[(cyclohexylmethoxy)carbonyl]-5'-deoxy-5-fluorocytidine,
5'-deoxy-5-fluoro-$N^4$-[(2-phenylethoxy)carbonyl]cytidine,
2',3'-di-O-acetyl-5'-deoxy-5-fluoro-$N^4$-(propoxycarbonyl)cytidine,
2',3'-di-O-acetyl-$N^4$-(butoxycarbonyl)-5'-deoxy-5-fluorocytidine,
2',3'-di-O-benzoyl-$N^4$-(butoxycarbonyl)-5'-deoxy-5-fluorocytidine,
2',3'-di-O-acetyl-5'-deoxy-5-fluoro-$N^4$-(pentyloxycarbonyl)cytidine,
2',3'-di-O-acetyl-5'-deoxy-5-fluoro-$N^4$-(isopentyloxycarbonyl)cytidine,
2',3'-di-O-acetyl-5'-deoxy-5-fluoro-$N^4$-(hexyloxycarbonyl)cytidine,
2',3'-di-O-acetyl-5'-deoxy-$N^4$-[(2-ethylbutyl)oxycarbonyl]-5-fluorocytidine,
2',3'-di-O-acetyl-$N^4$-[(cyclohexylmethoxy)carbonyl]-5'-deoxy-5-fluorocytidine,
2',3'-di-O-acetyl-5'-deoxy-5-fluoro-$N^4$-[(2-phenylethoxy)carbonyl]cytidine,
5'-deoxy-5-fluoro-$N^4$-(isobutoxycarbonyl)cytidine,
5'-deoxy-5-fluoro-$N^4$-[(2-propylpentyl)oxycarbonyl]cytidine,
5'-deoxy-$N^4$-[(2-ethylhexyl)oxycarbonyl]-5'-fluorocytidine,
5'-deoxy-5-fluoro-$N^4$-(heptyloxycarbonyl)cytidine,
$N^4$-[(2-cyclohexylethoxy)carbonyl]-5'-deoxy-5-fluorocytidine,
$N^4$-[(3-cyclohexylpropyl)oxycarbonyl]-5'-deoxy-5-fluorocytidine,
$N^4$-(cyclohexyloxycarbonyl)-5'-deoxy-5-fluorocytidine,
5'-deoxy-5-fluoro-$N^4$-[(3-phenylpropyl)oxycarbonyl]cytidine,
5'-deoxy-5-fluoro-$N^4$-[(2-methoxyethoxy)carbonyl]cytidine,
$N^4$-(butoxycarbonyl)-5'-deoxy-5-fluorocytidine and
5'-deoxy-5-fluoro-$N^4$-(pentyloxycarbonyl)cytidine.

4. A pharmaceutical composition comprising a therapeutically effective amount of one or more compounds of formula (I)

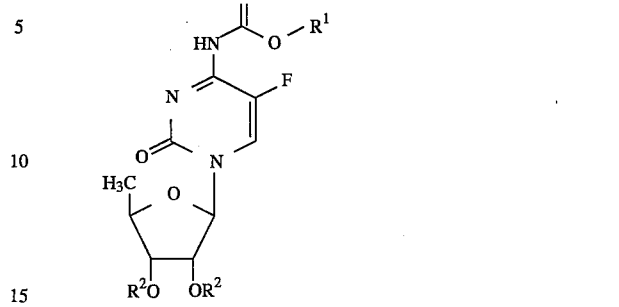

wherein $R^1$ is a saturated straight or branched hydrocarbon radical wherein the number of carbon atoms in the longest straight chain of the hydrocarbon radical ranges from three to seven, or is a radical of the formula —$(CH_2)_n$—Y wherein Y is a cyclohexyl radical, a $C_1$–$C_4$ alkoxy radical or a phenyl radical and wherein when Y is a cyclohexyl radical n is an integer from 0 to 4 and when Y is a $C_1$–$C_4$ alkoxy radical or a phenyl radical n is an integer from 2 to 4, and $R^2$ is a hydrogen atom or a radical easily hydrolyzable under physiological conditions, or a hydrate or solvate thereof, and an inert carrier.

5. A method of treating tumors comprising administering to a host in need of such treatment an effective amount of a compound of formula (I)

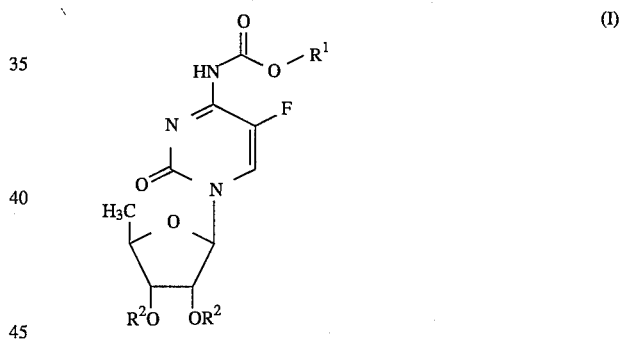

wherein $R^1$ is a saturated straight or branched hydrocarbon radical wherein the number of carbon atoms in the longest straight chain of the hydrocarbon radical ranges from three to seven, or is a radical of the formula —$(CH_2)_n$—Y wherein Y is a cyclohexyl radical, a $C_1$–$C_4$ alkoxy radical or a phenyl radical and wherein when Y is a cyclohexyl radical n is an integer from 0 to 4 and when Y is a $C_1$–$C_4$ alkoxy radical or a phenyl radical n is an integer from 2 to 4, and $R^2$ is a hydrogen atom or a radical easily hydrolyzable under physiological conditions, or a hydrate or solvate thereof.

6. The compound according to claim 1, 5'-deoxy-5-fluoro-$N^4$-(pentyloxycarbonyl)cytidine.

* * * * *